United States Patent
Andre et al.

(10) Patent No.: US 6,630,177 B1
(45) Date of Patent: *Oct. 7, 2003

(54) PRODUCTS EXTRACTED FROM A PLANT OF THE GENUS COMMIPHORA, PARTICULARLY THE COMMIPHORA MUKUL PLANT, EXTRACTS CONTAINING SAME AND APPLICATIONS THEREOF, FOR EXAMPLE IN COSMETICS

(75) Inventors: Patrice Andre, Neuvilles aux Bois (FR); Stéphane Lhermite, Semoy (FR); Françoise Pellicier, Loury (FR)

(73) Assignee: Parfums Christian Dior, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/352,939

(22) Filed: Jul. 14, 1999

Related U.S. Application Data

(63) Continuation of application No. 09/029,851, filed as application No. PCT/FR96/01415 on Sep. 13, 1996, now Pat. No. 5,972,341.

(30) Foreign Application Priority Data

Sep. 13, 1995 (FR) .............................. 95 10710

(51) Int. Cl.$^7$ ........................ A61K 35/78; A61K 31/22; A01N 25/00
(52) U.S. Cl. ...................... 424/748; 514/549; 514/844; 514/847
(58) Field of Search ............................ 424/195.15, 401, 424/725, 748, 195.18; 514/844, 846, 847, 944, 549; 560/174; 568/374

(56) References Cited

U.S. PATENT DOCUMENTS

| | | | | |
|---|---|---|---|---|
| 5,151,272 A | * | 9/1992 | Engstrom et al. | 424/450 |
| 5,273,747 A | * | 12/1993 | Bombardelli et al. | 424/195.1 |
| 5,521,223 A | * | 5/1996 | Piazza et al. | 514/785 |
| 5,690,948 A | * | 11/1997 | McCook et al. | 424/401 |
| 5,972,341 A | * | 10/1999 | Andre et al. | 424/195.1 |

* cited by examiner

*Primary Examiner*—Michael G. Hartley
(74) *Attorney, Agent, or Firm*—Dennison, Schultz & Dougherty

(57) ABSTRACT

Products of formula (I) extracted from a plant of the genus Commiphora, particularly the *Commiphora mukul* plant, wherein R is (a) a $CH_2OH$ grouping, (b) a COOH grouping, and salts or esters thereof are described. These products and the extracts containing them are effective cosmetic agents against wrinkles.

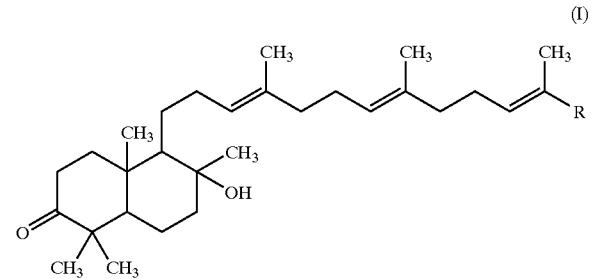

31 Claims, 1 Drawing Sheet

PRODUCTS EXTRACTED FROM A PLANT OF THE GENUS COMMIPHORA, PARTICULARLY THE COMMIPHORA MUKUL PLANT, EXTRACTS CONTAINING SAME AND APPLICATIONS THEREOF, FOR EXAMPLE IN COSMETICS

This application is a continuation of Ser. No. 09/029,851, filed May 20, 1998, now U.S. Pat. No. 5,972,341, which is a 371 of PCT/FR96/01415, filed Sep. 13, 1996.

The invention relates to the use in cosmetics of extracts of a plant of the genus Commiphora, particularly the plant *Commiphora mukul*, especially as an agent with antiwrinkle activity. It further relates, by way of novel industrial products, to two particularly active products isolated from these extracts, and to derivatives of these novel products.

It is known that the plant *Commiphora mukul* belongs to the family of the Burseraceae. *Commiphora mukul* is a plant of Indian origin which is very widely used in traditional Indian medicine and in ayurvedic medicine. A resin produced by *Commiphora mukul*, which is also called guggul, is used in particular in these applications. This ayurvedic treatment was known to comprise the treatment of obesity and lipidic disorders, as well as rheumatic diseases.

It should be noted that the term "guggul" denotes both the plant and the resin it produces. Also, this plant is a small tree or a shrub of 1.2 to 1.8 m in height, which grows essentially in India, and the gum resin can be harvested in the ordinary way by making an incision in the plant.

Patents U.S. Pat. No. 4,847,071, U.S. Pat. No. 4,847,069, U.S. Pat. No. 4,946,671 and U.S. Pat. No. 4,954,332 have recently described topical compositions, containing free radical absorbers and an anti-inflammatory agent, for protecting against UV radiation. Guggal or guggul extract is among the numerous anti-inflammatory agents mentioned.

Furthermore, document EP-A-513 671 has also disclosed compositions containing, as the active ingredient, a total lipophilic extract of the plant *Commiphora mukul*, which is obtained in particular from the resin of the bark of *Commiphora mukul*. This extract contains a high proportion of guggulsterones. This composition is described as having an anti-inflammatory, immunomodulating or antiandrogenic activity for the treatment of acne and benign hypertrophy of the prostate.

It has now been discovered, surprisingly and unexpectedly, that extracts of a plant of the genus Commiphora, particularly the plant *Commiphora mukul*, have an antiwrinkle activity and can thus be used as cosmetic agents for improving the surface appearance of the skin and particularly for reducing the depth of large wrinkles and eliminating small wrinkles.

On the basis of this discovery, the Applicant carried out complementary systematic studies aimed at identifying particularly active fractions responsible for this activity. It found in particular that these fractions contained two novel products which were particularly active as regards the activity in question. These products could be isolated and totally identified from extracts of the plant *Commiphora mukul*. They therefore constitute novel industrial products which have a remarkable activity as cosmetic agents for combating wrinkles.

The invention further relates to derivatives of the two novel products isolated according to the invention.

Thus, according to a first aspect, the invention relates to the products of formula (I):

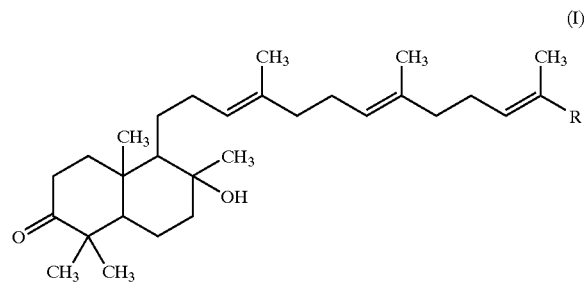

in which R is:

a) a C $H_2OH$ group or b) a COOH group, and their salts or esters.

The invention relates very particularly, by way of novel industrial products, to the products of formula (II):

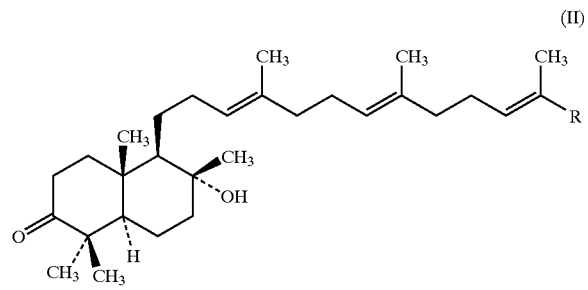

in which R is:

a) a $CH_2OH$ group, the product being denoted by formula $II_a$, b) a COOH group, the product being denoted by formula $II^b$, c) a group

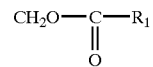

in which $R_1$ is a linear or branched alkyl group containing from 1 to 6 carbon atoms, particularly the methyl group, d) a group COOM, where M denotes an alkali metal, preferably sodium or potassium, or a quaternary ammonium or amine group, e) a group $COOM'_{0.5}$, where M' denotes an alkaline earth metal, preferably calcium, or f) a group $COOR_2$, where $R_2$ denotes a linear or branched alkyl group containing from 1 to 6 carbon atoms.

The invention relates very particularly to the two novel industrial products denoted respectively by $II_a$ and $II_b$ and having the following formulae:

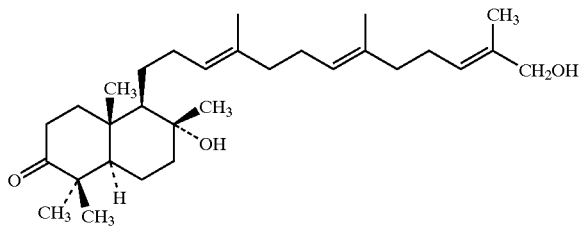

(IIa)

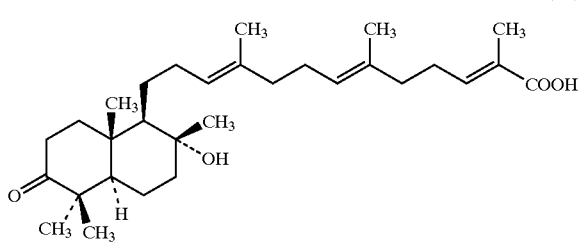

(IIb)

The two products could be isolated from the plant *Commiphora mukul* and were completely identified by different analytical techniques, as will become apparent from the following description.

The product of formula $II_a$, the empirical formula of which is $C_{30}H_{50}O_3$, will be referred to as "commipherol". Its nomenclature is as follows:

(5R, 10S,8R,9R)-3-oxopolypoda-13E,17E,21E-triene-8, 30-diol.

The acid derivative of formula $II_b$, the empirical formula of which is $C_{30}H_{48}O_4$, will be referred to as "commipherin". This is (5R,10S,8R,9R)-8-hydroxy-3-oxopolypoda-13E,17E,21 E-trien-30-oic acid.

The nomenclature used to denote the products of formulae $II_a$ and $II_b$ above is based on the name of the corresponding hydrocarbon; this is the triterpene α-polypodatetraene, which is well known in the literature, for example in the publication by Yoko Arai et al., Tetrahedron Letters, (1992) 33 (10) 1325–8, relating to the plant Polypodiodes formosane. The carbon atoms are numbered as indicated below:

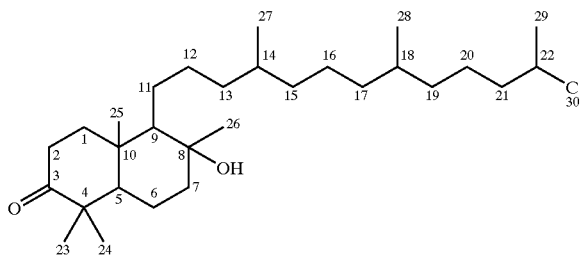

It should be noted that various triterpene derivatives possessing the polypodane carbon skeleton have been identified in other plants, particularly in ferns of the families of the Polypodiaceae, such as Polypodium vulgare, P. fauriei and P. virginianum (Y. Aral et al., Phytochemistry, (1991) 30 (10) 3369–3377; K. Shiojima et al., Tetrahedron Lett., (1983) 24, 5733), the Aspidiaceae (M. Nishizawa et al., J. Chem. Soc., Chem. Commun. (1984) no. 7, 467–8) and the Cheiropleuriaceae (R. Karnaya et al., Chem. Pharm. Bull. (1990) 38 (8) 2130–2).

According to a second aspect, the invention further relates to processes for the preparation of the two products $II_a$ and $II_b$ from the plant *Commiphora mukul*, as well as the acylation derivatives of the product $II_a$, particularly the acetylation product, and the salts and esters of the product $II_b$.

Different processes can be used to isolate the products of formulae $II_a$ and $II_b$ from the plant *Commiphora mukul*.

In these processes, it is advantageous to start from the resin of *Commiphora mukul*, which is subjected to different successive extraction and fractionation steps.

Thus, particularly advantageously, the resin of *Commiphora mukul* is subjected to a first so-called extraction step with a solvent or a mixture of solvents, after which the extract is subjected to different separation steps for isolating a particularly active fraction containing at least one of the products of the invention.

The first extraction step can be carried out using a wide range of solvents of very different polarities.

The following may be mentioned, in order of increasing polarity, as examples of solvents which can be used to carry out this step:

petroleum ether, with which 16% by weight of the crude resin can be extracted, dichloromethane, with which 26% by weight of the crude resin can be extracted, ethyl acetate, with which 30.5% by weight of the crude resin can be extracted, ethanol, with which 26.5% by weight of the crude resin can be extracted.

Figure 1:
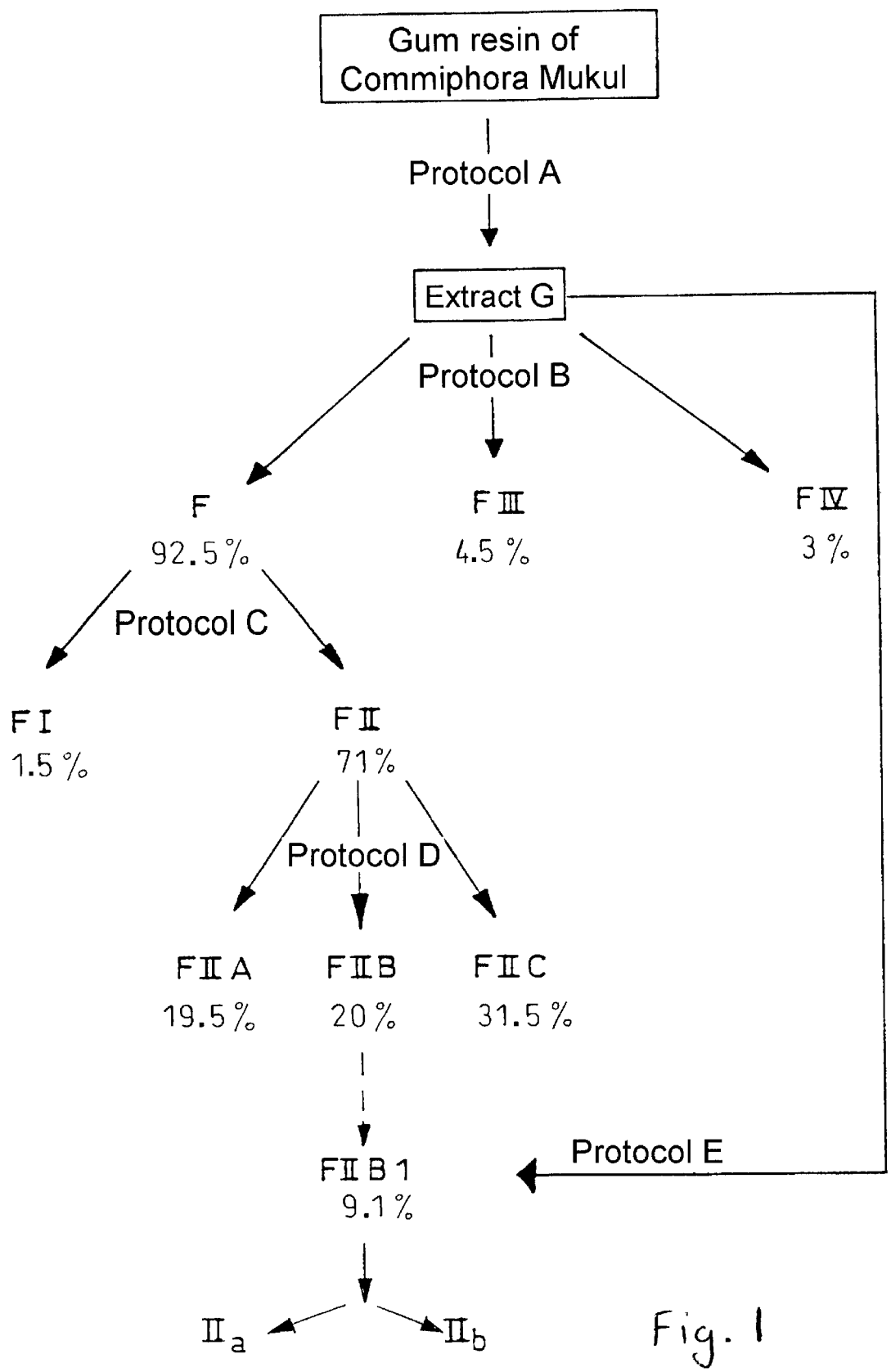
FIG. 1 schematically represents different protocols for preparing the products of formulae $II_a$ and $II_b$ from an extract of the resin of *Commiphora mukul* according to the invention.

According to the scheme of FIG. 1, a first extract according to the invention, called extract G, is prepared from the resin of *Commiphora mukul*.

This extract G is obtained by extraction of the resin with 96% ethanol at 45° C. after grinding of the aggregates.

In a first step, the extract G is subjected to a series of fractionations by high performance liquid chromatography. Each fraction is tested for its lipogenic activity on fibroblasts in culture using the method explained below. These different fractionations ultimately yield an active fraction, FIIB, whose characteristic peaks are identified on the chromatogram.

More precisely, in this first step, the extract G will be subjected initially to a protocol B for isolating the most active fractions, whereby high performance liquid chromatography makes it possible to separate the extract G into three fractions: F representing 92.5% of the extract G, FIII representing 4.5% of this extract, and FIV representing 3%. The fraction FIII could be identified as consisting essentially of sterols, and fraction FIV is composed essentially of the products resulting from the rinsing of the chromatography column with dichloromethane.

The fraction F is then subjected to protocol C for separation by liquid chromatography, which yields two fractions called FI and FII respectively. The fraction FI, which is substantially inactive, is discarded. It represents 21.5% of F and consists essentially of sterones (Z- and E-guggulsterone).

The fraction FII, which has a lipogenic activity, is in turn subjected to a fractionation by liquid chromatography, whereby it can be separated into three fractions: FIIA representing 19.5% of the extract G, FIIB representing 20% of the extract G, and FIIC representing 31.5% of the extract G. The fraction FIIB is the most active of these three fractions. The positions of the corresponding peaks are identified on the chromatogram.

It is then possible, in a second step, to obtain an active fraction called FIIB1, corresponding to the peaks of the fraction FIIB, directly from the extract G by fractionation according to protocol E.

The two products of formulae $II_a$ and $II_b$ can then be separated from the extract FIIB1 by preparative high performance liquid chromatography.

The two products $II_a$ and $II_b$, whose activities were found to be substantially equivalent, were perfectly purified and could be isolated by liquid chromatography under the following conditions:

Column: RP 18 Lichrospher 5 $\mu$m 125×4 mm

Mixtures: Water+0.1% $CF_3COOH$
  Acetonitrile

UV detection: $\lambda$=210 nm

The product of formula $II_a$ can then be subjected to a conventional acylation step, particularly acetylation step, in order to prepare the corresponding acylated derivatives, particularly the acetylated derivative.

The product $II_b$ can easily be converted to one of its salts, described above, by neutralization of the acid fraction at the end of the chain with a corresponding base.

Likewise, the esterification products of the product $II_b$ may easily be obtained by reacting it in conventional manner with a low molecular alcohol.

These reactions for acylating the product $II_a$ or esterifying or salifying the product $II_b$ can also be carried out directly on a mixture containing both the active products $II_a$ and $II_b$, particularly on the mixture FIIB1 described above.

For example, the acetylation of $II_a$ with acetic anhydride can be effected by treating the extract FIIB1 in the following manner: FIIB1 is dissolved in dichloromethane (1 volume), 1 volume of pyridine is added, followed by 1.2 equivalents of acetic anhydride per equivalent of FIIB1, and the reaction is allowed to proceed at room temperature overnight.

The Applicant found, totally surprisingly, that the extracts of the plant *Commiphora mukul*, especially the extracts particularly rich in products of formula $II_a$ or $II_b$, had a stimulating activity on lipogenesis inside the fibroblasts. This results in an increase in the cellular volume of the fibroblasts, leading to better contact with the extracellular protein network. This tones the dermis, making it possible to reduce the depth of the large and small wrinkles and, consequently, to make them less obvious. This activity therefore enabled the Applicant to propose a particularly novel solution for improving the surface appearance of the skin.

Thus, according to a third aspect, the invention relates to the use of at least one extract of a plant of the genus Commiphora, particularly the plant *Commiphora mukul*, as a cosmetic agent for modifying the surface of the skin by reducing the depth of the large and small wrinkles to give the skin a smoother appearance.

Different extracts of the plant *Commiphora mukul*, particularly extracts rich in compounds of formula I, II, $II_a$ or $II_b$, in a mixture thereof or in derivatives of these products, as defined above, may be used in this application.

In a first variant, the gum resin called guggul may be used as the extract of the plant *Commiphora mukul*.

In another variant, an extract obtained after grinding of the aggregates of the resin, followed by extraction with a solvent, is used as the extract of the plant *Commiphora mukul*. As seen above, a wide range of solvents may be used for this purpose.

However, referring to the classification of solvents by polarity, as published in particular by Veronika R. Meyer in Practical High-performance Liquid Chromatography (1988), John Wiley & Sons, pp. 120–121, solvents which will preferably be chosen are those whose polarity parameter p' is less than 5.5 and preferably between 0.1 and 4.5.

The above extract is advantageously obtained by extraction with an organic solvent or a mixture of organic solvents selected from the group consisting of n-pentane, n-hexane, petroleum ether, cyclohexane, n-decane, dichloromethane, isopropanol, n-propanol, chloroform, ethanol, ethyl acetate, acetone and methanol.

In other variants of the invention, the extract may be made up of different products which share the characteristic of being enriched in at least one of the products of formula I or II, particularly of formula $II_a$ or $II_b$, obtained from the extract described above.

As clearly illustrated in the examples given with reference to the scheme of FIG. 1, the products enriched in product(s) of the invention can be obtained for example from the extract G by subjecting this extract to different successive separation steps, especially involving high performance liquid chromatography or supercritical carbon dioxide extraction.

In one particularly advantageous variant of the invention, at least one of the products of formula I or II, particularly of formula $II_a$ or $II_b$, will be used as the cosmetic agent for modifying the surface of the skin as indicated above.

According to a fourth aspect, the invention further relates to a composition, in particular for cosmetic use, characterized in that it contains at least one of the products of formula I or II, particularly $II_a$ or $II_b$, or plant extracts containing at least one of these products, particularly extracts of a plant of the genus Commiphora and very particularly extracts of the plant *Commiphora mukul*, preferably in combination with an acceptable, in particular cosmetically acceptable, excipient or carrier.

Advantageously this composition contains from 0.001 to 1% by weight of at least one of the products of formula (I) or (II), particularly ($II_a$) or ($II_b$), preferably from 0.01 to 0.1%.

Alternatively this composition very advantageously contains from 0.005 to 5% by weight, preferably from 0.05 to 1% by weight, of an extract of *Commiphora mukul* containing at least one of the above-mentioned products, particularly an extract of the resin of this plant.

The cosmetic compositions of the invention can be in different forms, in particular in the form of solutions, milks, gels or creams.

In one variant of the invention, the cosmetic composition also contains a cosmetically effective amount of a product acting on fibronectin synthesis and/or collagen synthesis.

Examples which may be mentioned of products acting on fibronectin synthesis are galactolipids and particularly galactosylglycerides, the use of which is 30 described in the French patent application filed on Feb. 15, 1995 under the number 95.01714, which has not yet been published.

Vitamin C may be mentioned as an example of a product acting on collagen synthesis.

The invention further relates to a method of cosmetic treatment for modifying the surface of the skin by reducing the depth of the large and small wrinkles to give the skin a smoother appearance, characterized in that an effective amount of a product or a plant extract containing said product is applied to the areas of skin to be treated, particularly to the face, in order to obtain said surface modification, said product or said extract preferably being incorporated in a cosmetically acceptable excipient.

In one variant of this method of cosmetic treatment, the above-mentioned plant extract is an extract of the plant Commiphora mukul.

Other characteristics and advantages of the invention will become apparent from the following Examples, which are given purely in order to illustrate the invention.

EXAMPLES

Example 1

Preparation of the Extract G According to the Invention

This extract is prepared by extraction of the resin of *Commiphora mukul* after grinding of the aggregates.

The extract is produced with 96% ethanol at 45° C. in the following manner: 10 g of resin and 200 ml of ethanol are introduced into a 500 ml round-bottomed flask fitted with a condenser and a stirrer and heated by means of a heating plate.

Stirring and extraction take a minimum of 2 h, but it is advisable to allow 4 to 5 h in order to improve the yield.

Extraction is followed by filtration and then by evaporation under vacuum.

The extraction yield is about 25% by weight.

Example 2

Preparation of the Fraction FIIB1 From the Extract G

This Example is given with reference to the scheme of FIG. 1. Table 1 below gives details of protocols B, C, D and E as regards the nature and characteristics of the chromatography columns used, the type of detector and the nature of the eluents used.

Example 3

Preparation of the Products $II_a$ and $II_b$ From the Fraction FIIB1

The two products $II_a$ and $II_b$ were separated by preparative liquid chromatography and purification on a C18 column using isocratic elution by the recycling technique. The products $II_a$ and $II_b$ can be visualized by detection at 210 nm.

The two products of formulae $II_a$ and $II_b$ were totally identified by mass spectrometry, which made it possible to verify the empirical formulae established by NMR.

The results obtained by carbon NMR for the two products $II_a$ and $II_b$ are given in Tables 2 and 3 below:

TABLE 2

Chemical shifts of the different hydrocarbon groups of the product $II_a$

| Atom no. | $^{13}C$ δ ppm | Multiplicity |
|---|---|---|
| 1 | 38.35 | $CH_2$ |
| 2 | 34.02 | $CH_2$ |
| 3 | 217.16 | Cquat |
| 4 | 47.57 | Cquat |
| 5 | 55.18 | CH |
| 6 | 21.41 | $CH_2$ |
| 7 | 43.80 | $CH_2$ |
| 8 | 73.82 | Cquat |
| 9 | 60.36 | CH |
| 10 | 39.39 | Cquat |
| 11 | 25.80 | $CH_2$ |
| 12 | 31.20 | $CH_2$ |
| 13 | 124.83 | CH |
| 14 | 135.47 | Cquat |
| 15 | 39.34 | $CH_2$ |
| 16 | 26.33 | $CH_2$ |
| 17 | 124.54 | CH |
| 18 | 134.68 | Cquat |
| 19 | 39.67 | $CH_2$ |
| 20 | 26.16 | $CH_2$ |
| 21 | 126.04 | CH |
| 22 | 134.71 | Cquat |
| 23 | 21.41 | $CH_3$ |
| 24 | 26.33 | $CH_3$ |
| 25 | 14.89 | $CH_3$ |
| 26 | 23.62 | $CH_3$ |
| 27 | 16.06 | $CH_3$ |
| 28 | 16.27 | $CH_3$ |
| 29 | 13.77 | $CH_3$ |
| 30 | 68.97 | $CH_2$ |

TABLE 1

| | Commiphora mukul | | | |
|---|---|---|---|---|
| | Product to be purified | Column | Detector | Eluent | Fractions obtained |
| Protocol B | extract G | kromasil 100 C18 150 × 21.7 mm 13 μm | 220 nm | methanol | F, FIII, FIV |
| Protocol C | fraction F | kromasil 100 C18 150 × 21.7 mm 13 μm | 210 nm | methanol/ water gradient | FI, FII |
| Protocol D | fraction FII | kromasil 100 C18 150 × 21.7 mm 13 μm | 210 nm | methanol/ water gradient | FIIA, FIIB, FIIC |
| Protocol E | extract G | kromasil 100 C18 150 × 21.7 mm 13 μm | light scattering detector (LSD) | methanol/ water gradient | FIIB1 |

TABLE 3

Chemical shifts of the different hydrocarbon groups of the product $11_b$

| Atom no. | $^{13}C$ δ ppm | Multiplicity |
|---|---|---|
| 1 | 38.28 | $CH_2$ |
| 2 | 34.02 | $CH_2$ |
| 3 | 217.10 | Cquat |
| 4 | 47.57 | Cquat |
| 5 | 55.18 | CH |
| 6 | 21.35 | $CH_2$ |
| 7 | 43.59 | $CH_2$ |
| 8 | 74.54 | Cquat |
| 9 | 60.48 | CH |
| 10 | 39.39 | Cquat |
| 11 | 25.85 | $CH_2$ |
| 12 | 31.44 | $CH_2$ |
| 13 | 125.15 | CH |
| 14 | 134.71 | Cquat |
| 15 | 39.38 | $CH_2$ |
| 16 | 26.28 | $CH_2$ |
| 17 | 125.47 | CH |
| 18 | 134.55 | Cquat |
| 19 | 38.03 | $CH_2$ |
| 20 | 25.92 | $CH_2$ |
| 21 | 143.82 | CH |
| 22 | 133.43 | Cquat |
| 23 | 21.41 | $CH_3$ |
| 24 | 26.33 | $CH_3$ |
| 25 | 14.89 | $CH_3$ |
| 26 | 23.54 | $CH_3$ |
| 27 | 16.09 | $CH_3$ |
| 28 | 15.88 | $CH_3$ |
| 29 | 12.27 | $CH_3$ |
| 30 | 171.14 | Cquat |

Example 4

Supercritical $CO_2$ Extraction

Extraction is carried out in the following two steps on about 240 g of ground crude resin:

Step 1:

This step is performed in a conventional apparatus with pure $CO_2$ at 150 bar and 40° C.

The $CO_2$ consumption is 2000 kg of $CO_2$ for 24 kg of resin to be extracted.

The extraction yield is about 12.50% based on the initial batch. The extract obtained is discarded.

Step 2:

This step is performed in the same apparatus with a mixture containing 98% by weight of 98% $CO_2$ and 2% by weight of ethanol.

1000 kg of $CO_2$ are used for 24 kg of crude resin (i.e. 18 kg of $CO_2$ for 240 g of resin).

The extraction yield is about 10% based on the initial batch. This gives a so-called SFE (supercritical fluid extraction) enriched in molecules $II_a$ and $II_b$ with a concentration factor of 6 to 8 relative to the crude resin.

Example 5

Demonstration of the Activity of the Extracts and Products According to the Invention 1. Culture The cells used are 3T3 F442A, which constitute a line of murine preadipocytes selected for their ability to convert to adipocytes if the culture conditions allow, in accordance with the method of Green, H. & Kehinde, C., Cell 1 (1974) 113.

This line actually constitutes a model for studying the differentiation of adipocytes in vitro.

As a monolayer during the multiplication phase, 3T3 F442A have the morphology and enzymatic characteristics of fibroblasts.

The initially confluent cells cease to divide in order to enter their early differentiation phase. This differentiation leads to the formation of colonies of cells which undergo conversion to adipocytes.

This differentiation is accompanied by changes in the biosynthesis of several proteins and by an increase in different enzymatic activities (acetyl CoA carboxylase, ATP citrate lyase, fatty acid synthetase, phosphoenolpyruvate kinase and glycero-3-phosphate dehydrogenase, called $G_3PDH$).

The aim was to measure the expression of two differentiation markers, namely glycero-3-phosphate dehydrogenase ($G_3PDH$) on the one hand and cyclic AMP (cAMP) on the other.

It is pointed out here that the enzyme $G_3PDH$ allows the formation, in the fibroblast, of glycerol 3-phosphate, a molecule which is subsequently involved in the synthesis of the intracellular lipids (triglycerides). Thus an increase in the activity of the $G_3PDH$ is directly linked to an increase in this synthesis.

Furthermore, it is known that the amount of cAMP, an intracellular mediator, increases during the intracellular lipolysis reaction. The cAMP formed in the cell is then excreted thereby into the extracellular medium. Thus a decrease in the cAMP content of the culture medium represents a decrease in the degradation of the triglycerides and hence an intracellular accumulation of these lipids.

The resin of *Commiphora mukul* (extract G), the fraction FIIB1 and the products $II_a$ and $II_b$ were therefore studied with these two differentiation markers.

The fibroblasts are inoculated at the bottom of Petri dishes of diameter 35 mm in Dulbecco's Modified Eagle's Medium (DMEM), in the presence of 5% of calf serum (CS) and 5% of fetal calf serum (FCS). Each experiment is performed in triplicate.

During the treatment phase, the medium consists of DMEM+10% of fetal calf serum.

The product or extract according to the invention is dissolved in ethanol and used on the cultures at a final concentration of 5 µg/ml.

The culture operations are carried out as follows:

On day D=0: inoculation in DMEM+5% CS, 5% FCS

On day D+2: change of medium

On day D+5: treatment with resin of *Commiphora mukul* (extract G), FIIB1 or $II_a$ or $II_b$ at 5 µg/ml in DMEM, 10% FCS On day D+6: assay of cAMP in culture medium On days D+7 and D+9: treatment identical to that performed on D+5

On day D+12: grinding of the cells for assay of $G_3PDH$.

2. Assay of the Cyclic adenosine 3.5-Monophosnhate (cAMP)

The assay of the cAMP, which is performed by radioimmunoassay or RIA (kit from Immunotech, a French Company, reference 1117), is based on the principle of antigen-antibody competition. The samples and standards are incubated, in the presence of cAMP radiolabeled with iodine 125, in tubes where anti-cAMP antibodies have been fixed beforehand.

After incubation, the contents of the tubes are sucked out and the residual radioactivity is counted with a gamma counter. A standard curve is prepared with 6 known concentrations of cAMP and the concentration of the samples is defined by means of this calibration curve.

As the cAMP is produced and excreted by the cells, one is therefore measuring the cAMP contained in the culture medium. More precisely, one is measuring the amount of cAMP excreted into the culture medium in 24 hours.

3. Determination of the Glycero-3-phosilhate Dehydrogenase ($G_3PDH$) Activity

The cellular monolayer is recovered by scraping and vigorously homogenized in TRIS-HCl buffer (25 mM, pH 7.4), 1 mM EDTA, at 4° C. The $G_3PDH$ activity is determined on the supernatant of the ground cellular material immediately after centrifugation.

$G_3PDH$ catalyzes the following reaction:

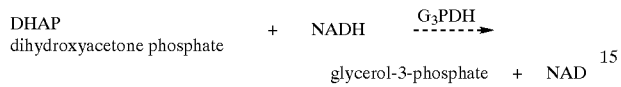

DHAP + NADH $\xrightarrow{G_3PDH}$ glycerol-3-phosphate + NAD
dihydroxyacetone phosphate The conversion of the coenzyme NADH (hydrogenated nicotinamide adenine dinucleotide) to NAD as a function of time, which represents the rate of the enzymatic reaction and hence the activity of the enzyme $G_3PDH$, is measured by spectrophotometry at 340 nm.

It is possible to calculate an absorption difference (ΔAbs)/min, which corresponds to the initial rate of the enzymatic reaction.

The results are expressed in terms of specific activity, i.e. in nmol of NADH converted/min/mg of cellular proteins (the total cellular protein content is evaluated by the method of BCA—PIERCE: protein assay reagent).

4.1. $G_3PDH$ Activity

The experimental results of the evaluation of the activity of the enzyme $G_3PDH$ are shown in Table 4 below.

The activity $A_1$ of the products according to the invention on stimulation of the activity of this enzyme is calculated according to the following formula:

$$A_1 = \frac{V_p - V_t}{V_t} \times 100$$

in which:

$V_p$ is the mean value, over the three experiments, of the rate of conversion of NADH, expressed in nmol/min/mg of cellular proteins, in the cultures treated with the products according to the invention, $V_t$ is the mean value of this rate in the control cultures.

TABLE 4

| Cultures | Rate of conversion of NADH nmol/min/mg of proteins | Activity $A_1$ % |
|---|---|---|
| Control cultures | 49.6 ± 3.39 | 0 |
| Extract G | 156 ± 43 | 215 |
| Fraction FIIB1 | 242 ± 42 | 394 |
| $II_a$ | 222 ± 88 | 348 |
| $II_b$ | 352 ± 62 | 610 |

It is therefore very clear from Table 4 that the products according to the invention, whether they be the extract G, the fraction FIIB1 or the products $II_a$ or $II_b$, very greatly increase the activity of the enzyme $G_3PDH$ in the fibroblast cultures, compared with the activity of this enzyme in the control cultures. In fact, it is seen that the activity of this enzyme is increased 3-fold by the action of the extract G and 7-fold by the action of the compound $II_b$. Thus it is demonstrated that the products according to the invention contribute to a substantial increase in the synthesis of intracellular triglycerides.

4.2. Assay of cAMP

The quantity of cAMP excreted in 24 hours into the medium of the different cultures prepared is shown in Table 5. It is expressed in nmol/liter of medium. The activity $A_2$ of the products according to the invention on the excretion of cAMP by the cells, which is directly related to the intracellular lipolysis reaction, is calculated according to the following formula:

$$A_2 = \frac{q_p - q_t}{q_t} \times 100$$

in which:

$q_p$ represents the mean quantity, over the three experiments, of cAMP excreted into the medium of the cultures treated with the products according to the invention, expressed in nmol/liter/24 hours, $q_t$ represents this mean quantity in the case of the control cultures.

TABLE 5

| Cultures | cAMP excreted nmol/liter/24 hours | $A_2$ % |
|---|---|---|
| Control cultures | 66 ± 3.5 | 0 |
| Extract G | 56.8 ± 3.8 | −13.9 |
| FIIB1 | 42 ± 2 | −36.4 |

These results given in Table 5 show that the quantity of cAMP excreted into the culture medium is smaller in the case of the cultures treated with the products of the invention than in the case of the control cultures.

Thus, in the cells of the treated cultures, it is apparent that the lipolysis is very considerably reduced compared with that which occurs in the cells of the control cultures.

In conclusion, these experiments clearly demonstrate that the products according to the invention act via two complementary routes to increase the quantity of intracellular lipids, on the one hand by favoring their synthesis, which is demonstrated by the increase in the activity of the enzyme $G_3PDH$, and on the other hand by limiting their degradation, which is demonstrated by the reduction in the cAMP content of the treated cultures.

It will moreover be observed that the two molecules $II_a$ and $II_b$ give the best results and in fact appear to be the basis of the lipogenic activity of the extracts and fractions according to the invention.

Thus the products according to the invention accelerate the adipocyte differentiation in the fibroblasts. Furthermore, because of the accumulation of the lipids, these cells increase in volume and thus allow better contact with the extracellular protein network, thereby consolidating the dermis. The result of this tonicity of the dermis is to decrease the depth of large and small wrinkles and give the surface of the skin a smoother appearance.

Example 6

Antiwrinkle Cream

An antiwrinkle cream is prepared by mixing the constituents below, given with their percentages by weight based on the final composition, in accordance with the following preparative protocol:

A mixture A consisting of:

| | |
|---|---|
| Brij 72 ® | 0.8 |
| Brij 721 ® | 2.2 |
| Tegin 90 ® | 1.7 |
| Stearyl alcohol | 1.8 |
| Stearine | 3.0 |
| Silicone oil (Fluid 200 ®) | 0.20 |
| Squalane | 10.0 |
| Miglyol 812 ® | 10.0 |
| D,L-α-Tocopherol acetate | 0.2 |
| Phénonip | 0.5 |
| SFE of Example 4 | 0.5 | is prepared.

A mixture B consisting of:

| | |
|---|---|
| A: | |
| Glycerol | 5.00 |
| Water | 58.53 |
| Carbopol 940 | 0.20 |
| is added | |
| and then C, D and E consisting respectively of: | |
| C: 10% sodium hydroxide solution | 0.07 |
| D: Wheat proteins | 5.00 |
| E: Perfume | 0.30 | are added.

Example 7

Eye Contour Gel with Antiwrinkle Activity

A composition is prepared by mixing the components A, B, C, D and E below, the constituents of which are given with their percentages by weight based on the final composition.

| | |
|---|---|
| A: | |
| Carbopol 1342 ® | 0.40 |
| Water | 83.20 |
| B: 10% sodium hydroxide solution | 0.40 |
| C: | |
| Product II$_a$ according to the invention | 0.1 |
| Miglyol 829 ® | 10.00 |
| Phénonip | 0.50 |
| D,L-α-Tocopherol acetate | 0.20 |
| D: Wheat proteins | 5.00 |
| E: Perfume | 0.20 |

What is claimed is:

1. A method for cosmetic skin care, comprising applying to areas of the skin in need thereof an effective amount of an anti-wrinkle agent consisting essentially of at least one extract of a plant of the genus Commiphora for promoting stimulation of synthesis of intracellular triglycerides or promoting inhibition or lowering degredation of intracellular triglycerides, and thereby reducing depth of large and small wrinkles and giving the skin a smooth appearance.

2. The method of claim 1, wherein said extract of a plant of the genus Commiphora is an extract of the plant *Commiphora mukul*.

3. The method according to claim 1, wherein said extract is an extract of the resin of the plant *Commiphora mukul*.

4. The method according to claim 3, wherein said extract is obtained by grinding resin aggregates followed by extraction with a solvent having a polarity p' less than 5.5.

5. The method according to claim 4, wherein the solvent used to perform the extraction is selected from the group consisting of n-pentane, n-hexane, petroleum ether, cyclohexane, n-decane, dichloromethane, isopropanol, n-propanol, chloroform, ethanol, ethyl acetate, acetone and methanol.

6. The method according to claim 1, wherein said extract is obtained by extraction of *Commiphora mukul* with carbon dioxide in a supercritical state.

7. The method according to claim 1, wherein said extract is enriched in at least one product of formula (I):

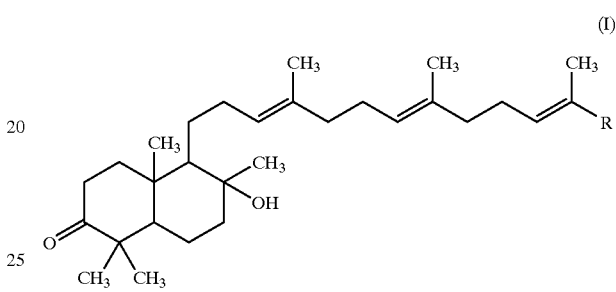

(I)

in which R is:
a) a $CH_2OH$ group or
b) a COOH group,
and salts and esters thereof.

8. The method according to claim 7, wherein said extract is enriched in a product of formula (II):

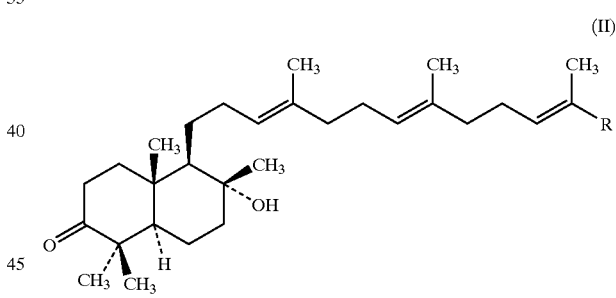

(II)

in which R is:
a) a $CH_2OH$ group, the product being denoted by formula II$_a$,
b) a COOH group, the product being denoted by formula II$_b$,
c) a group

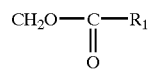

in which $R_1$ is a linear or branched alkyl group of 1 to 6 carbon atoms,
d) a group COOM, where M is an alkali metal,
e) A group $COO(M'_{0.5'})$ where M' is an alkaline earth metal, or
f) a group $COOR_2$, where $R_2$ is a linear or branched alkyl group containing from 1 to 6 carbon atoms.

9. The method according to claim 8, wherein said extract is enriched in a product of formula (II$_a$):

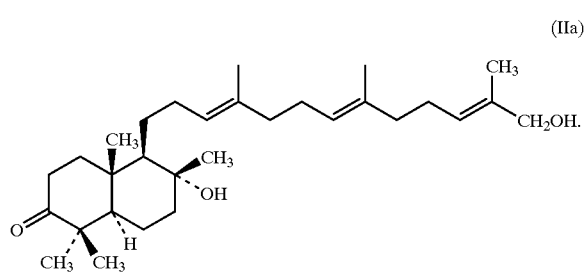

10. The method according to claim 8, wherein said extract is enriched in a product of formula (II$_b$):

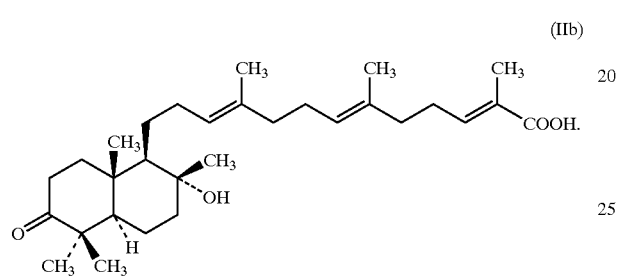

11. The method according to claim 7, wherein said composition contains from 0.001 to 1% by weight of said product of formula (I).

12. The method according to claim 7, wherein said composition comprises from 0.005 to 5% by weight of said enriched extract.

13. The method according to claim 12, wherein said enriched extract is an extract of resin of *Commiphora mukul*.

14. A method for cosmetic skin care, comprising application to an area of the skin in need thereof an effective amount of at least one product of formula (I):

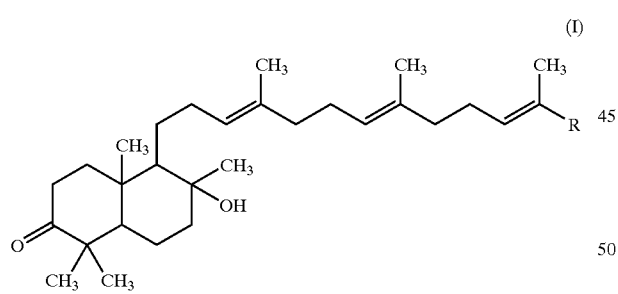

in which R is:
a) A CH$_2$OH group or
b) a COOH group,
and salts and esters thereof,
wherein said effective amount is applied by means of a cosmetic composition comprising from 0.005 to 5% by weight of an anti-wrinkle agent consisting essentially of an extract of *Commiphora mukul* containing said product of formula (I) in an amount sufficient for promoting stimulation of synthesis of intracellular triglycerides or promoting inhibition or lowering degradation of intracellular triglycerides, and thereby reducing depth of large and small wrinkles and giving the skin a smooth appearance.

15. A cosmetic composition comprising 0.001 to 1% by weight of at least one compound selected from the group consisting of:

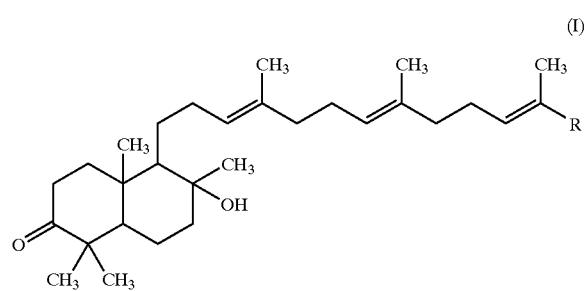

in which R is:
a) a CH$_2$OH group or
b) a COOH group, and

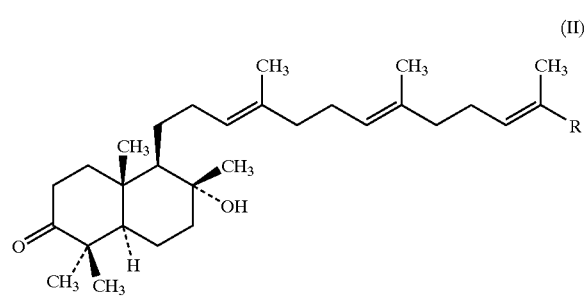

in which R is:
a) a CH$_2$OH group,
b) a COOH group,
c) a group

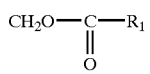

in which R$_1$ is a linear or branched alkyl group containing from 1 to 6 carbon atoms,
d) a group COOM, where M is an alkali metal,
e) a group COOM'$_{0.5}$, where M' is an alkaline earth metal, or
f) a group COOR$_2$ where R$_2$ is a linear or branched alkyl group containing from 1 to 6 carbon atoms, and salts and esters thereof, said compound having been obtained by process steps comprising treating resin of *Commiphora mukul* by extraction with an organic solvent to prepare an extract G, subjecting said extract G to at least one fractionation step in order to isolate a fraction consisting essentially of at least one product of formula I or formula II, with a cosmetically acceptable excipient.

16. The composition according to claim 15, comprising 0.01 to 0.1% of said at least one compound.

17. The composition according to claim 15, wherein said at least one compound is selected from the group consisting of:

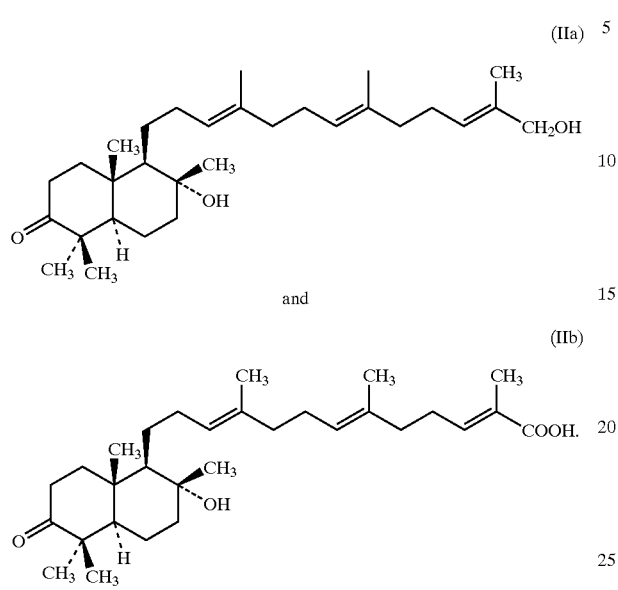

18. The composition according to claim 15, containing 0.005 to 5% by weight of an extract of *Commiphora mukul* containing said at least one compound.

19. The composition according to claim 18, containing 0.05 to 1% by weight of said extract.

20. The composition according to claim 15, additionally comprising a cosmetically effective amount of a product acting on fibronectin synthesis, a product acting on collagen synthesis, or a mixture thereof.

21. The composition according to claim 20, wherein the product acting on fibronectin synthesis is selected from the group consisting of galactolipids, galactoglycerides and mixtures thereof.

22. The composition according to claim 20, wherein the product acting on collegen synthesis is vitamin C.

23. A cosmetic composition comprising a plurality of anti-wrinkle active agents, one of said agents comprising 0.001 to 1% by weight of at least one compound selected from the group consisting of:

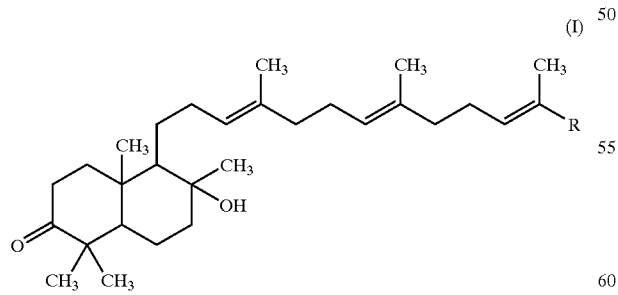

in which R is:

a) a CH$_2$OH group or b) a COOH group, and

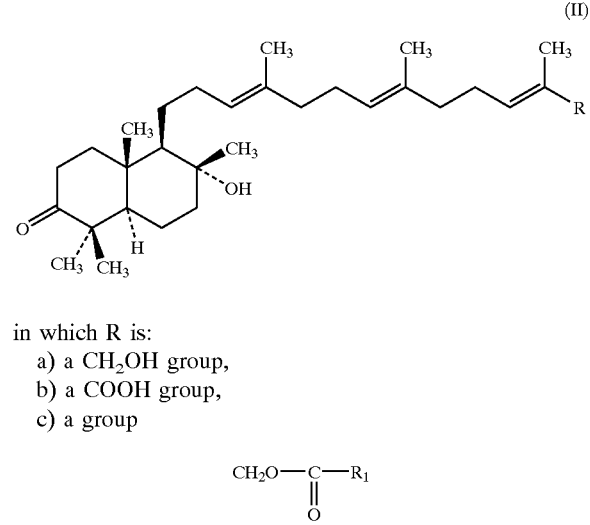

in which R is:
a) a CH$_2$OH group,
b) a COOH group,
c) a group $$CH_2O-\underset{\underset{O}{\|}}{C}-R_1$$

in which $R_1$ is a linear or branched alkyl group of 1 to 6 carbon atoms,
d) a group COOM, where N is an alkali metal,
e) a group COO(M'$_{0.5}$), where M' is an alkaline earth metal, or
f) a group COOR$_2$, where R$_2$ is a linear or branched alkyl group containing from 1 to 6 carbon atoms,
and salts and esters thereof,
said compound having been obtained by process steps comprising treating resin of *Commiphora mukul* by extraction with an organic solvent to prepare an extract G, subjecting said extract G to at least one fractionation step in order to isolate a fraction consisting essentially of at least one product of formula I or formula II, and a cosmetically acceptable excipient.

24. The composition according to claim 23, additionally comprising a cosmetically effective amount of a product acting on fibronectin synthesis, a product acting on collagen synthesis, or a mixture thereof.

25. The composition according to claim 24, wherein the product acting on fibronectin synthesis is selected from the group consisting of galactolipids, galactoglycerides and mixtures thereof.

26. The composition according to claim 24, wherein the product acting on collegen synthesis is vitamin C.

27. A cosmetic composition comprising an anti-wrinkle agent consisting essentially of at least one compound selected from the group consisting of:

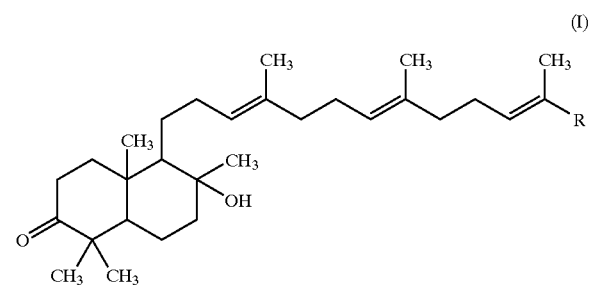

in which R is:
a) a CH$_2$OH group or b) a COOH group, and

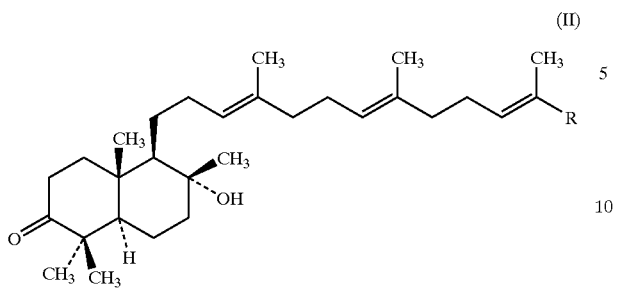

(II)

in which R is:
a) a CH$_2$OH group,
b) a COOH group,
c) a group

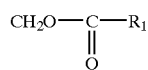

in which R$_1$ is a linear or branched alkyl group of 1 to 6 carbon atoms,
d) a group COOM, where M is an alkali metal,
e) a group COO(M'$_{0.5}$), where M' is an alkaline earth metal, or
f) a group COOR$_2$, where R$_2$ is a linear or branched alkyl group containing from 1 to 6 carbon atoms,
and salts and esters thereof,
said compound having been obtained by process steps comprising treating resin of *Commiphora mukul* by extraction with an organic solvent to prepare an extract G, subjecting said extract G to at least one fractionation step in order to isolate a fraction consisting essentially of at least one product of formula I or formula II, said at least one compound being present in said composition in an amount of 0.001 to 1% by weight, and
optionally, a cosmetically effective amount of a compound acting on fibronectin synthesis, a compound acting on collagen synthesis, or a mixture thereof,
with a cosmetically acceptable excipient.

28. The composition according to claim 27, wherein the product acting on fibronectin synthesis is selected from the group consisting of galactolipids, galactoglycerides and mixtures thereof.

29. The composition according to claim 27, wherein the product acting on collegen synthesis is vitamin C.

30. A method for cosmetic skin care, comprising applying to areas of the skin in need thereof an effective amount of an anti-wrinkle agent consisting essentially of a compound for improving fibronectin synthesis and at least one extract of a plant of the genus Commiphora for promoting stimulation of synthesis of intracellular triglycerides or promoting inhibition or lowering degradation of intracellular triglycerides, and thereby reducing depth of large and small wrinkles and giving the skin a smooth appearance.

31. A method for cosmetic skin care, comprising applying to areas of the skin in need thereof an effective amount of an anti-wrinkle agent consisting essentially of a compound for improving collagen synthesis and at least one extract of a plant of the genus Commiphora for promoting stimulation of synthesis of intracellular triglycerides or promoting inhibition or lowering degradation of intracellular triglycerides, and thereby reducing depth of large and small wrinkles and giving the skin a smooth appearance.

* * * * *